United States Patent
Reed et al.

(10) Patent No.: US 8,043,295 B2
(45) Date of Patent: Oct. 25, 2011

(54) VERTEBRAL SPREADING INSTRUMENT COMPRISING MARKERS

(75) Inventors: Pete Reed, Cincinnati, OH (US); Claus Schaffrath, München (DE); Gerhard Kleinszig, Buch (DE); Gunther Becht, Dornach (DE)

(73) Assignee: Brainlab AG, Feldkirchen (DE)

( * ) Notice: Subject to any disclaimer, the term of this patent is extended or adjusted under 35 U.S.C. 154(b) by 1412 days.

(21) Appl. No.: 11/260,507

(22) Filed: Oct. 27, 2005
(Under 37 CFR 1.47)

(65) Prior Publication Data

US 2006/0264963 A1 Nov. 23, 2006

Related U.S. Application Data

(60) Provisional application No. 60/645,399, filed on Jan. 19, 2005.

(30) Foreign Application Priority Data

Oct. 27, 2004 (EP) .................................... 04025566

(51) Int. Cl.
*A61B 17/58* (2006.01)
(52) U.S. Cl. ........................................ 606/90; 606/86 R
(58) Field of Classification Search .................. 606/90, 606/99, 105, 86 R, 914–916, 205–209; 600/424, 600/426
See application file for complete search history.

(56) References Cited

U.S. PATENT DOCUMENTS

| | | | | |
|---|---|---|---|---|
| 3,750,652 | A | * | 8/1973 | Sherwin .......................... 606/90 |
| 3,960,147 | A | * | 6/1976 | Murray ............................ 606/75 |
| 5,213,112 | A | * | 5/1993 | Niwa et al. ..................... 600/587 |
| 5,769,861 | A | | 6/1998 | Vilsmeier |
| 6,261,296 | B1 | | 7/2001 | Aebi et al. |
| 6,340,363 | B1 | | 1/2002 | Bolger et al. |
| 6,351,659 | B1 | | 2/2002 | Vilsmeier |
| 6,478,800 | B1 | | 11/2002 | Fraser et al. |
| 6,498,944 | B1 | * | 12/2002 | Ben-Haim et al. ............. 600/407 |
| 6,739,068 | B1 | | 5/2004 | Rinner |
| 7,608,078 | B2 | * | 10/2009 | Berry ........................... 606/86 A |
| 7,635,369 | B2 | * | 12/2009 | Cinquin et al. .................. 606/90 |
| 2002/0095081 | A1 | | 7/2002 | Vilsmeier |

(Continued)

FOREIGN PATENT DOCUMENTS

DE 195 36 180 A1 6/1997

(Continued)

OTHER PUBLICATIONS

European Search Report for corresponding Application No. 04025566.3 dated Apr. 4, 2005.

*Primary Examiner* — Eduardo C Robert
*Assistant Examiner* — Jan Christopher Merene
(74) *Attorney, Agent, or Firm* — Renner, Otto, Boisselle & Sklar, LLP

(57) ABSTRACT

A vertebral spreading instrument for moving apart two vertebrae of a spine includes a plurality of spreading fingers and a spreading mechanism for adjusting a distance between the spreading fingers. The spreading mechanism includes a first and a second part, the first and second parts each including a respective marker trackable by a navigation system. Relative positions of the first and second parts change when the distance between the spreading fingers is adjusted, and different relative positions are unequivocally assigned to different distances of the spreading fingers.

15 Claims, 3 Drawing Sheets

U.S. PATENT DOCUMENTS

| | | | |
|---|---|---|---|
| 2003/0220650 A1* | 11/2003 | Major et al. | 606/90 |
| 2003/0236447 A1 | 12/2003 | Ritland | |
| 2005/0004450 A1* | 1/2005 | Ben-Haim et al. | 600/424 |
| 2005/0182416 A1* | 8/2005 | Lim et al. | 606/90 |
| 2005/0203539 A1* | 9/2005 | Grimm et al. | 606/99 |
| 2006/0009780 A1* | 1/2006 | Foley et al. | 606/99 |
| 2006/0052793 A1* | 3/2006 | Heinz | 606/90 |
| 2006/0074431 A1* | 4/2006 | Sutton et al. | 606/90 |
| 2006/0074432 A1* | 4/2006 | Stad et al. | 606/90 |
| 2006/0149277 A1* | 7/2006 | Cinquin et al. | 606/90 |
| 2006/0235423 A1* | 10/2006 | Cantu | 606/90 |
| 2006/0241641 A1* | 10/2006 | Albans et al. | 606/90 |
| 2006/0241643 A1* | 10/2006 | Lim et al. | 606/90 |

FOREIGN PATENT DOCUMENTS

| | | |
|---|---|---|
| DE | 196 39 615 A1 | 4/1998 |
| DE | 296 23 941 U1 | 12/2000 |
| EP | 1 454 589 A1 | 8/2004 |
| WO | 03/092507 A2 | 11/2003 |

* cited by examiner

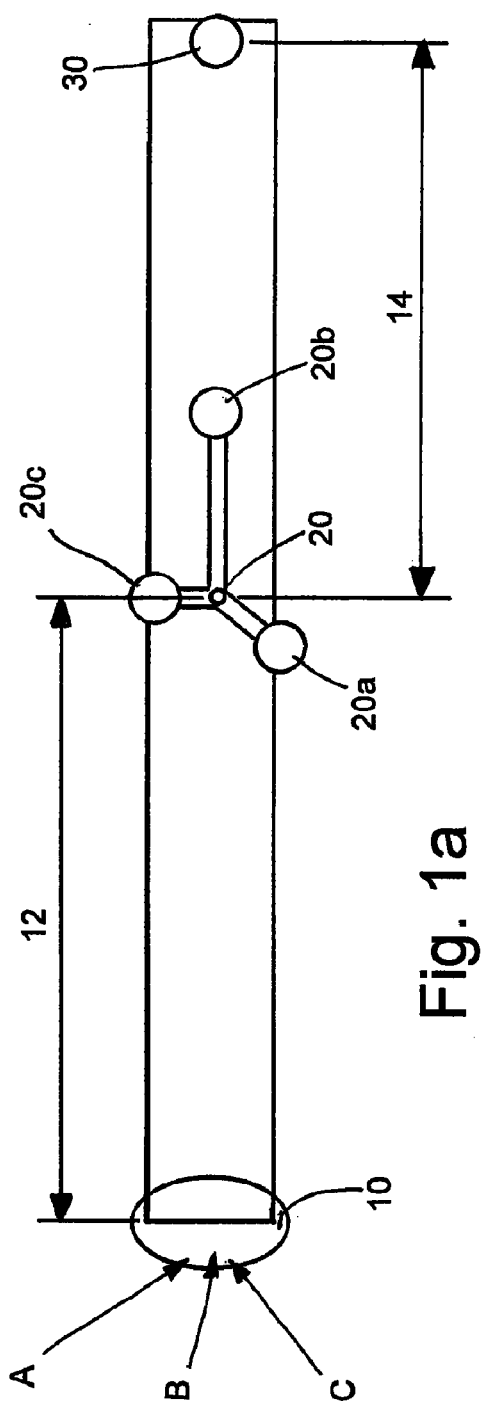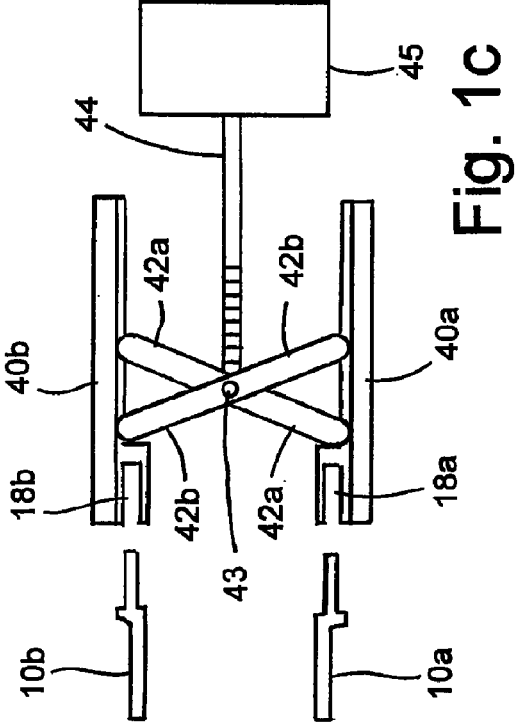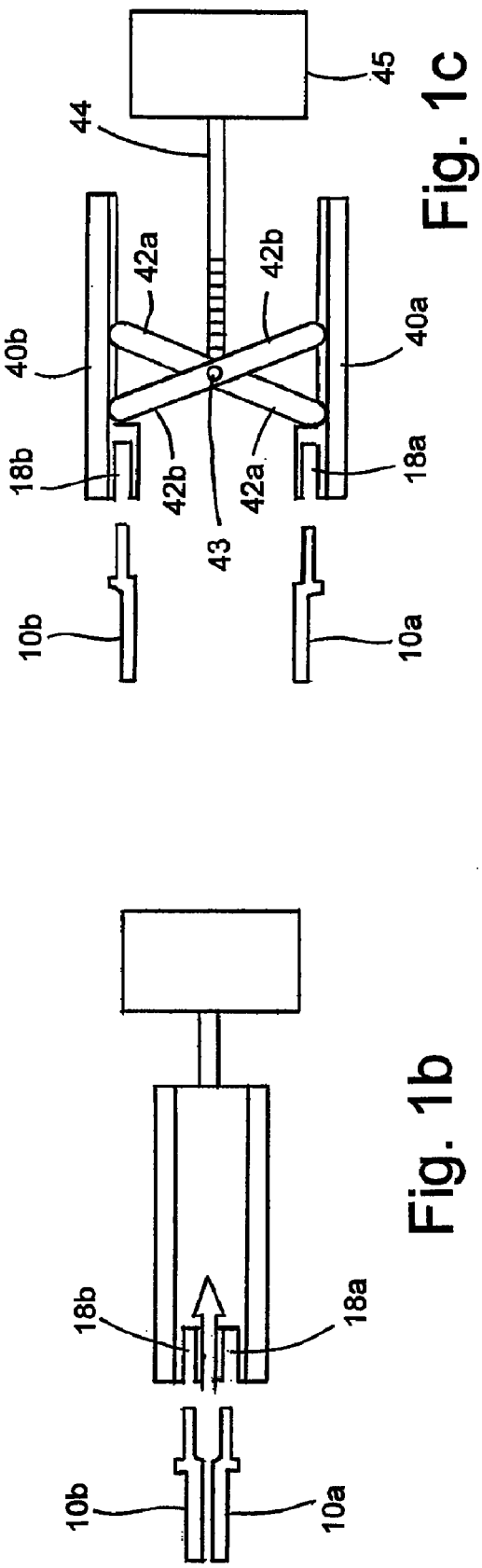

VERTEBRAL SPREADING INSTRUMENT COMPRISING MARKERS

RELATED APPLICATION DATA

This application claims priority of U.S. Provisional Application No. 60/645,399 filed on Jan. 19, 2005, which is incorporated herein by reference in its entirety. European Patent Application No. 04025566.3 is hereby incorporated herein by reference in its entirety.

FIELD OF THE INVENTION

The present invention relates to the vertebrae and, more particularly, to a vertebral spreading instrument for moving apart or spreading two vertebrae of a spine via two spreading fingers.

BACKGROUND OF THE INVENTION

A vertebral spreading instrument is known, for example, from U.S. Pat. No. 6,478,800 B1, the disclosure of which is incorporated herein by reference in its ventirety. As disclosed in U.S. Pat. No. 6,478,800, two vertebrae can be spread by two fingers or blade tips and, via a sliding or pusher rod, an artificial intervertebral disc can be slid between the blade tips and into the free space created by spreading the vertebrae. Thus, U.S. Pat. No. 6,478,800 B1 discloses a possible embodiment of a spreading mechanism that operates such that the two spreading fingers or blades are each extensions of a lever arm that can be pivoted about a common bearing. The artificial intervertebral disc can be pinched between the two lever arms and situated distal to the bearing, wherein the lever arms reduce their distance in the distal direction.

The distance between the lever arms thus becomes smaller as they are situated closer to the spine. If the distal intervertebral disc then is shifted further in the distal direction, it thus forces the two lever arms apart. This results in two vertebrae of the intervertebral discs being spread, such that the artificial intervertebral disc can be slid into a free space between the two vertebrae by the spreading fingers or blades. The free space between the vertebrae is a result of a previously performed surgical removal of the damaged intervertebral disc.

A vertebral spreading instrument also is known from U.S. Pat. No. 6,261,296 B1, the contents of which is incorporated herein by reference in its entirety. The vertebral spreading instrument includes a scissor-like vertebral spreading mechanism, wherein two limbs or extensions are arranged such that they can rotate about an axis (e.g., an axis formed by a bolt coupling the extensions together), thereby providing a scissor-like motion. Proximal handles diverge in the proximal direction, and by pressing the handles together, spreading fingers at the distal end of the scissor-shaped spreading instrument move apart as the extensions rotate about the axis. The distance between the spreading fingers can be set at the proximal end of the spreading instrument via a setting screw that connects the two handles at the proximal end of the spreading mechanism.

SUMMARY OF THE INVENTION

A vertebral spreading instrument enables two vertebrae of a spine to be moved or spread apart by means of two spreading fingers. The spreading fingers can be part of a spreading mechanism that serves to adjust a distance between the spreading fingers. The spreading fingers can be a distal end of the spreading mechanism. Preferably, the spreading fingers are designed to be discoid or cuneiform.

The spreading mechanism can include a first part and a second part, wherein relative positions of the first and second part with respect to each other change when the distance between the spreading fingers is changed. The change in relative positions can be a function of the change in distance between the spreading fingers, such that a change in the distance between the spreading fingers can be deduced from a particular change in the relative position of the first and second parts. The spreading mechanism can be configured such that an absolute distance between the spreading fingers can be deduced from the relative position of the first and second parts. The relative position thus can be a function of the distance between the spreading fingers. In other words, a predetermined distance or relative position of the two spreading fingers with respect to each other can be unequivocally (bijectively) assigned to each of the various relative positions that the first and second part can assume with respect to each other.

At least one marker can be attached to the first part and at least one marker can be attached to the second part. The first and second parts can be selected such that a change in their positions with respect to each other is a function of the change in distance between the spreading fingers. Thus, a distance or relative position between the two spreading fingers can be unequivocally (bijectively) assigned to each relative position between the first and second part. A change in the relative position between the first and second part can be a function of the change in distance between the two spreading fingers.

Using the aforesaid arrangement, it is possible to deduce the distance between the spreading fingers by detecting the position of the first and second markers. More specifically, a known geometry of the vertebral spreading instrument can be used in conjunction with the position of the first and second markers to deduce the distance between spreading fingers. The distance between the spreading fingers can be calculated based on the known relative positions and/or distances between the spreading fingers and the markers. In particular, the relationship between the various relative positions of the first and second markers and the various distances can be known in advance (e.g. as a table or mathematical function).

At least two other markers can be provided on the vertebral spreading instrument. This allows not only the distance between the spreading fingers to be determined by detecting the markers but, also the absolute position of the spreading fingers in a space monitored by cameras to be determined. To this end, three of the at least four markers preferably span a plane and, more particularly, the at least four markers can span a three-dimensional space. A reference star can be provided that includes three of the at least four markers. The reference star can be attached to the first part, wherein the positional relationship between the two spreading fingers and the first part can be known in advance, so as to deduce the absolute spatial position of the two spreading fingers by detecting the reference star. In particular, the movement of the vertebral spreading instrument can be tracked spatially by detecting the reference star. The distance between the markers of the reference star and the spreading fingers at a pre-set distance between the spreading fingers, in particular a zero distance, preferably is known in advance. The at least three markers of the reference star can have a known and fixed relative position that is not changed by the spreading procedure.

Alternatively, two of the markers can be provided on the first part in a fixed pre-set positional relationship and two of the markers can be provided on the second part in a fixed pre-set positional relationship. In this way, the position of the vertebral spreading instrument and the spreading fingers can be spatially tracked, and the distance between the spreading fingers determined.

The markers can be passive markers that reflect detection beams or detection waves. The detection beams or detection waves can be electromagnetic radiation, such as visible, infrared or UV light. The detection waves also can be sound waves such as, for example, ultrasound waves.

The detectors can be appropriate detectors for the corresponding detection beams and detection waves, e.g., cameras that can measure light (UV, visible, infrared light, etc.) or sound detectors. The detectors can be arranged such that they can detect all markers attached to the vertebral spreading instrument (e.g., the detection beams and/or detection waves emitted by them) and can determine the spatial position of the markers by evaluating the detection results.

The markers also can be active markers that actively emit the aforesaid detection beams or detection waves. The aforesaid cameras represent examples of detection means for detecting the detection beams and/or detection waves.

Markers, reference stars and navigation systems used in the invention are disclosed, for example, in DE 195 36 180 A1, DE 296 23 941 U1 and DE 196 39 615 A1, which correspond to U.S. Pat. Nos. 5,769,861, 6,351,659 B1 and US 2002-095081 A1. The content of the aforesaid documents is incorporated herein by reference in their entirety.

At least four markers can be provided to spatially determine the distance between the spreading fingers and the position of the vertebral spreading instrument. At least one of the markers (and preferably all of the markers) can be arranged proximal to the spreading fingers, and can be arranged at the proximal end of the vertebral spreading instrument, thereby not restricting movement at the distal end. The first part can be arranged on a part or section of the vertebral spreading instrument (the spreading mechanism) that is not moved when the spreading mechanism is activated to adjust the spreading distance, (e.g., a portion or part of the instrument that does not experience a change in position due to the spreading procedure or motion). In other words, the position of the first part can be independent of the distance between the spreading fingers and may not be influenced by the change in distance of the spreading fingers. The first part of the spreading mechanism can be situated on a section designed as a rotational joint, wherein two limbs or extensions rotate about the rotational joint and the spreading fingers are situated at each end of said limbs or extensions. The first part also can be positionally fixed with respect to said rotational joint, e.g., the first part's position does not change with respect to the rotational joint. In particular, the first part can represent a section, and the spreading fingers can rotate about the section. The first part also can be positionally fixed with respect to a geometric focus of the spreading fingers.

The second part can be attached proximal to the first part. In this way, the markers do not restrict the area to be operated on. The second part can be a part that experiences a change in position when the distance between the spreading fingers is changed. In particular, the second part can be connected, mechanically motion-coupled, to at least one of the spreading fingers or can be integral with at least one of the spreading fingers. If two limbs or extensions are rotated about a rotational point to obtain the spreading motion, then the second part can be arranged in a section proximal to the rotational point, wherein the second part experiences a rotation by an angle that corresponds to or is a function of an angle by which a spreading finger rotates about the rotational point.

The first part can be a part of the spreading mechanism or vertebral spreading instrument that connects an arm on which the first spreading finger can be situated with an arm on which the second spreading finger can be situated. The second part can be not only a rotational joint, but, in another embodiment, a lever fulcrum that serves as the fulcrum for a rocking movement of two limbs or extensions. A spreading finger can be situated at the end of each limb or exension, such as is described in U.S. Pat. No. 6,478,800, wherein the limbs rock about the lever fulcrum, for example. The vertebral spreading mechanism can also be designed to be scissor-like, such as described in U.S. Pat. No. 6,261,296 B1, for example.

The spreading mechanism also can be designed in the manner of a jack (e.g., a scissor jack), wherein two limbs or extensions are connected by a turnstile and one of the spreading fingers is situated at the end of each limb or extension. By rotating a thread, the two limbs or extensions are moved apart or together (in particular, moved apart or together in parallel) in accordance with a jack principle. The first part can be situated on sections that do not change their position when the thread is rotated. The first part thus can be arranged on the thread bearing, can be positionally fixed, or can be positionally fixed with respect to a geometrical focus of the two spreading fingers. The second part can be a section that travels when the thread is rotated, e.g., moves relative to the geometrical focus of the two spreading fingers. In this case, the second part can be arranged proximal to the focus of the turnstile or the first part. The first part can be arranged on a casing, wherein the thread can be mounted such that it can rotate with respect to the casing. The second part can travel relative to the casing when the thread is rotated, and can be designed such that it is moved lineally, e.g., in a straight line, wherein the distance traveled can be a function of the distance between the spreading fingers.

The vertebral spreading instrument can be designed such that it includes a disc holder to hold an artificial intervertebral disc. The disc holder can be designed separately from the spreading fingers and can be moved independently from the spreading fingers, as is known, for example, from U.S. Pat. No. 6,478,800, or at least one of the spreading fingers, and preferably both of the spreading fingers, is/are designed as a disc holder.

In the following, an embodiment is described wherein the spreading fingers are designed as disc holders. To this end, recesses can be provided in the spreading fingers, and, when the two spreading fingers assume a pre-set distance, an artificial intervertebral disc can be inserted into the recesses using an exact fit and/or held using a press fit. Thus, the artificial intervertebral disc can be held or clamped between the two spreading fingers. Since the position of the spreading fingers can be known or determined on the basis of the markers, the position of the artificial intervertebral disc also can be known or determined. This enables the practitioner to insert the artificial intervertebral disc between two vertebrae of a spine.

Alternatively, a separate disc holder can be provided that holds the artificial intervertebral disc when the fingers are spread. This separate disc holder can be designed such that it allows the intervertebral disc to be shifted in the distal direction. The separate disc holder can be designed such that the disc can be shifted linearly in a plane situated centrally between the spreading fingers. To this end, a guiding rod can be provided that is arranged centrally between the limbs or extensions at the ends of which the spreading fingers are situated. A marker also can be attached to the separate disc holder to determine the position of the artificial intervertebral disc on the basis of the known distance between the end at which the artificial intervertebral disc is situated and the marker, wherein the separate disc holder can be moved in a known direction relative to the vertebral spreading instrument, so as to determine the absolute position of the artificial intervertebral disc.

The vertebral spreading instrument can be used as part of an instrument navigation system that includes cameras or other detection means for determining a position of the markers in three-dimensional space. If passive markers are provided, then means can be arranged for emitting detection beams or detection waves, in particular illuminating means that irradiate and/or illuminate the passive markers such that the beams can reflect onto the detection means (in particular cameras or light sensors). A computer also can be provided to calculate the position of the markers in three-dimensional space from the detected radiation.

The forgoing and other embodiments of the invention are hereinafter discussed with reference to the drawings.

BRIEF DESCRIPTION OF THE DRAWINGS

FIG. 1a schematically shows an arrangement of markers on an exemplary vertebral spreading instrument in accordance with the invention.

FIGS. 1b-1c schematically illustrate a spreading mechanism of the instrument of FIG. 1 in accordance with the invention.

DETAILED DESCRIPTION

Figure 2C:
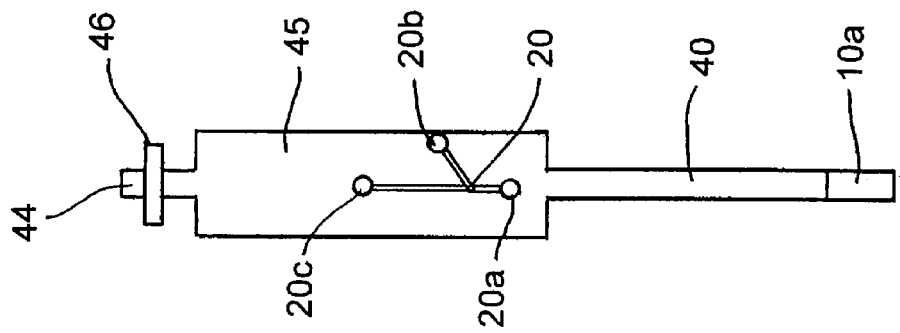
FIGS. 2a-2c show various views of another exemplary vertebral spreading instrument in accordance with the invention.

FIG. 1a shows a marker arrangement in a vertebral spreading instrument, wherein a tip includes spreading fingers 10. Various artificial intervertebral discs A, B and C can be attached at the spreading fingers 10. More particularly, the spreading fingers 10 preferably are designed such that various artificial intervertebral discs A, B or C can be attached so as to enable use of the vertebral spreading instrument with a high degree of flexibility. The spreading fingers 10 are situated at a fixed distance 12 away from a reference star 20, which includes three marker spheres 20a, 20b and 20c. An additional marker is indicated by 30 and is situated at a variable distance 14 from the reference star 20. The distance 14 varies with the distance between the spreading fingers 10.

FIGS. 1b and 1c show an exemplary spreading mechanism according to the invention that operates in accordance with a jack principle (e.g., a scissor jack). FIG. 1b shows spreading fingers 10a and 10b, which can be detachably inserted into corresponding cavities 18b and 18a. In this way, different spreading fingers 10 can be used in accordance with the desired requirements. In particular, different spreading fingers 10 can be selected in accordance with the artificial intervertebral disc to be used.

As shown in FIG. 1c, the cavities 18b and 18a are respectively connected to two limbs or extensions 40b and 40a, which can be moved apart in parallel. A turnstile 42 that includes arms 42a and 42b is connected to the limbs 40a and 40b. The arm 42b, for example, is connected to the limb 40b such that it can rotate and can slide in a longitudinal direction of the instrument in a rail within the limb 40a. Correspondingly, the arm 42a, for example, is connected to the limb 40a such that it can rotate and can slide in a rail within the limb 40b.

The arms 42a and 42b are connected to each other, such that they can rotate via a rotational joint 43. One end of the threaded rod 44 is connected to the rotational joint 43. The threaded rod 44 rotates in an inner thread of the casing 45 and can thus be shifted in the longitudinal direction relative to the casing 45 (e.g., a first part). The inner thread thus serves as a bearing for the threaded rod. The limbs 40a and 40b have a pre-set distance from the casing 45 due to a distance holder (not shown) and cannot move in the longitudinal direction but rather only towards and away from each other. If the rotational joint 43 (e.g., a second part) is then moved away from the casing, the limbs 40a and 40b are moved apart. If the rotational joint 43 is drawn towards the casing by the threaded rod 44, the limbs 40a and 40b are moved towards each other. The casing is positionally fixed with respect to a geometrical focus of the two spreading fingers and, in particular, does not change its position when the distance between the spreading fingers is changed. The casing serves as the first part of the vertebral spreading instrument.

Figure 2B:
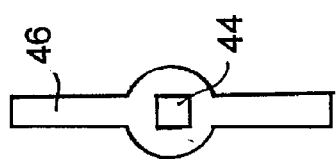
Figure 2A:
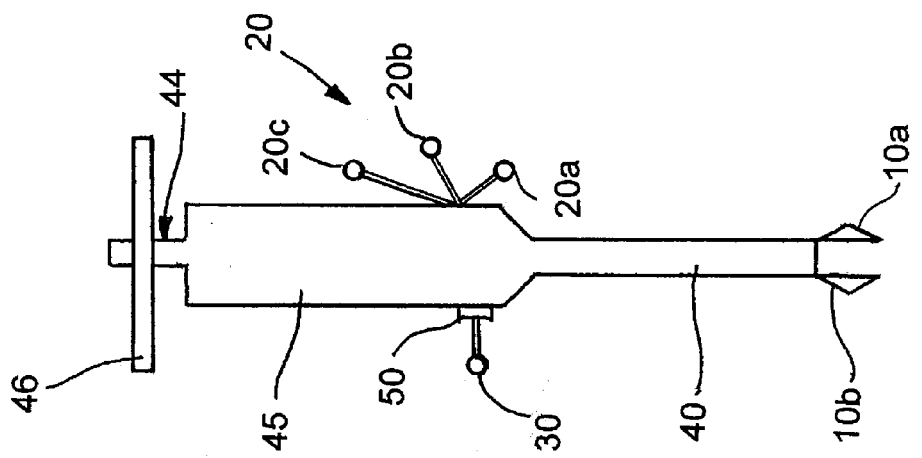

FIGS. 2a-2c shows an embodiment that uses the mechanism of FIGS. 1b and 1c. Identical reference numerals in FIGS. 2a-2c indicate the same parts as in FIG. 1. The limbs 40a and 40b are indicated in general by 40, since they are adjacent to each other. The threaded rod 44 protrudes at the proximal end of the casing 45. The threaded rod 44 can be rotated in the casing 45 using a handle 46, which is connected and rotationally fixed to the threaded rod 44, such that the threaded rod 44 travels in the longitudinal direction of the casing. This drives the limbs 40 apart, as explained above with respect to FIGS. 1b and 1c. An indicator 50, to which the marker 30 is attached, is connected to the threaded rod 44. The indicator 50 serves as the second part of the vertebral spreading instrument and can travel in a gap in the casing (not shown). The indicator 50 is connected to the threaded rod 44 such that indicator 50 participates in the movement of the threaded rod 44. The position of the indicator 50 in the gap (not shown) thus reflects the distance between the spreading fingers 10a and 10b. The reference star 20, including the markers 20a, 20b and 20c, is situated opposite the indicator 50 with the marker 30. The reference star 20 is fixedly connected to the casing 45 and thus does not travel with the rotational movement of the threaded rod 44.

FIG. 2b shows a view from the proximal end of the vertebral spreading instrument. FIG. 2c shows a lateral view of FIG. 2a.

Figure 3:
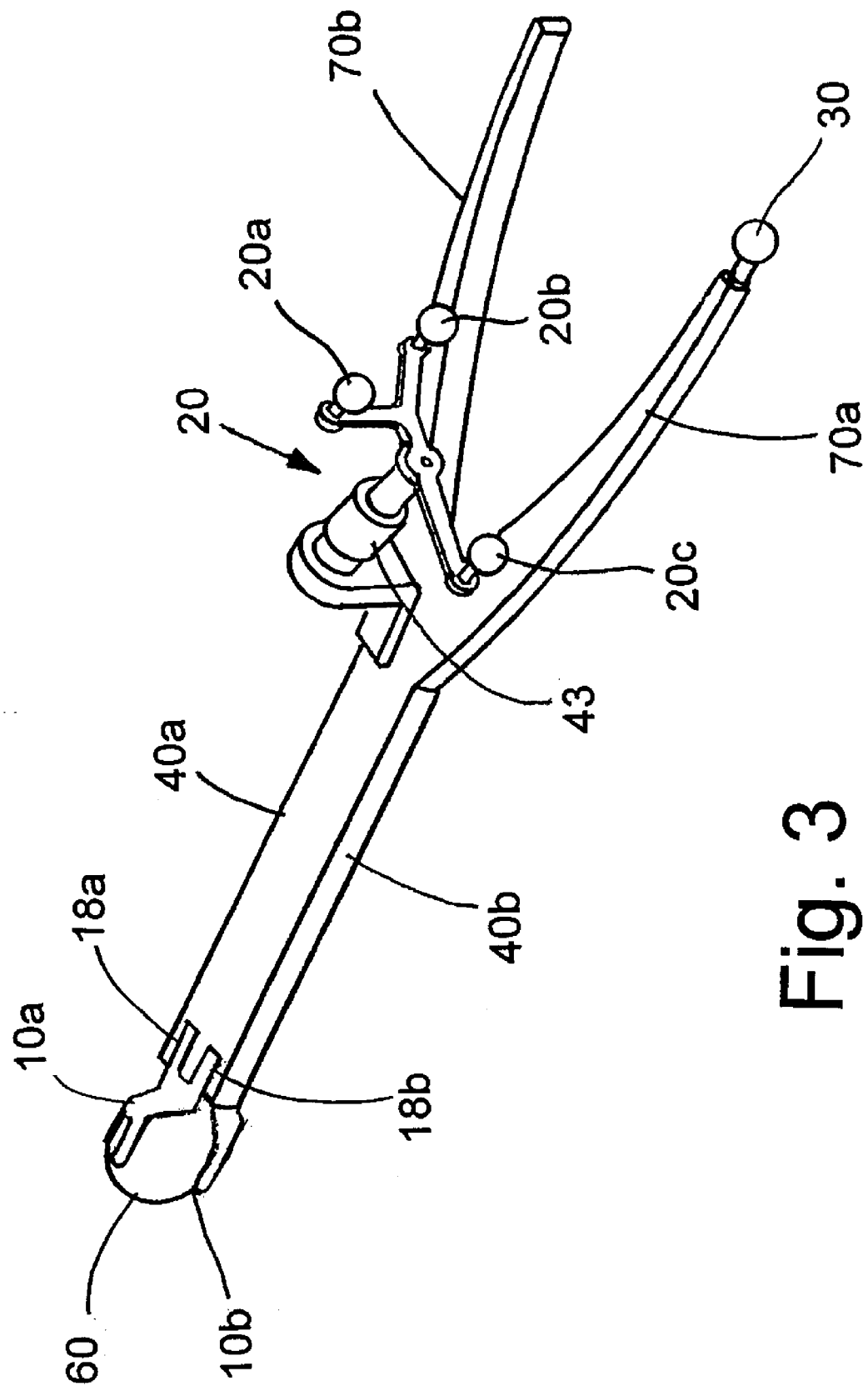
FIG. 3 shows a perspective view of yet another exemplary vertebral spreading instrument in accordance with the invention.

FIG. 3 shows another vertebral spreading instrument according to the invention. Functionally identical parts are again provided with the same reference numerals. An artificial intervertebral disc 60 is held by the spreading fingers 10a and 10b. The spreading finger 10a is inserted into a cavity 18a of the limb 40a. The spreading finger 10b is correspondingly inserted into a cavity 18b of the limb 40b. Thus, the spreading fingers again can be exchanged according to requirement. In particular, the spreading fingers 10a and 10b can comprise different receptacles for artificial intervertebral discs. Since the spreading fingers 10a and 10b can be exchanged, intervertebral discs having any shape and thickness can thus be used.

As in the embodiment in FIGS. 1a-1c, the distance between the spreading fingers again results from the relative position between the marker 30 and the reference star 20. The marker 30 is situated on an arm 70a, which is rigidly connected to the limb 40a and rotates together with the limb 40a about a rotational joint 43. This applies correspondingly to the arm 70b, which is rigidly connected to the limb 40b and rotates about the same rotational joint 43. The reference star 20 is arranged positionally fixed with respect to the rotational joint 43. By rotating the arms 70a and 70b about the rotational joint 43, the practitioner can move the limbs 40a and 40b and, therefore, the spreading fingers 10a and 10b apart. The position of the marker 30 relative to the reference star 20 is changed by moving the arms 70a and 70b apart. This change is a function of the distance between the spreading fingers 10a and 10b. The distance between the spreading fingers 10a and 10b can thus be exactly determined by measuring the markers 20a, 20b, 20c and 30.

The embodiments shown in FIGS. 2a-2c and 3 thus allow the distance between the spreading fingers 10a and 10b to be determined by determining the position of the reference star 20 relative to the marker 30. In particular, determining the distance between the spreading fingers 10a and 10b by inserting templates into the intermediate space between the vertebrae is thus no longer necessary, and surgery is thus made easier.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A vertebral spreading instrument for moving apart two vertebrae of a spine, comprising:
   a plurality of spreading fingers;
   a spreading mechanism for adjusting a distance between the spreading fingers, wherein the spreading mechanism includes a first and a second part, said first and second parts each including a respective marker trackable by a navigation system and configured to reflect or emit detection beams or detection waves, and at least two additional markers configured to reflect or emit detection beams or detection waves,
   wherein relative positions of the first and second parts change when the distance between the spreading fingers is adjusted, and different relative positions are unequivocally assigned to different distances of the spreading fingers via the markers on the first or second parts; and
   wherein the first part includes a gap such that when moving the second part the marker on the second part moves along the gap.

2. The vertebral spreading instrument as set forth in claim 1, further comprising a reference star provided on the first part, said reference star comprising the marker included on the first part and at least two of the at least two additional markers.

3. The vertebral spreading instrument as set forth in claim 1, wherein the first part is a section of the spreading mechanism that does not change position when the distance between the spreading fingers is adjusted.

4. The vertebral spreading instrument as set forth in claim 1, wherein the second part is situated proximal to the first part.

5. The vertebral spreading instrument as set forth in claim 1, wherein the spreading mechanism is configured such that the second part travels a path in a straight line along a longitudinal axis of the spreading instrument when the distance between the spreading fingers is adjusted, a length of said path being a function of the change in distance.

6. The vertebral spreading instrument as set forth in claim 1, wherein the second part is a rotational joint or a lever fulcrum.

7. An instrument navigation system, comprising:
   a vertebral spreading instrument for moving apart two vertebrae of a spine, comprising:
   a plurality of spreading fingers;
   a spreading mechanism for adjusting a distance between the spreading fingers, wherein the spreading mechanism includes a first and a second part, said first and second parts each including a respective marker trackable by a navigation system and configured to reflect or emit detection beams or detection waves,
   wherein relative positions of the first and second parts change when the distance between the spreading fingers is adjusted, and different relative positions are unequivocally assigned to different distances of the spreading fingers via the markers on the first or second parts;
   wherein the first part includes a gap such that when moving the second part the marker on the second part moves along the gap; and
   a detection device for detecting detection beams or waves reflected or emitted by the markers, wherein the detection device is arranged such that it can determine a spatial position of the markers.

8. The vertebral spreading instrument as set forth in claim 1, wherein the spreading mechanism includes a plurality of cavities, and wherein the spreading fingers are configured to be detachably inserted into respective ones of the plurality of cavities.

9. The vertebral spreading instrument as set forth in claim 8, further comprising limbs, wherein the limbs are operatively coupled to the second part.

10. The vertebral spreading instrument as set forth in claim 9, wherein the limbs are arranged a pre-set distance from the first part and are configured to maintain the pre-set distance from the first part as the limbs move relative to each other.

11. The vertebral spreading instrument as set forth in claim 1, wherein the first part includes a casing that is positionally fixed with respect to a geometrical focus of the spreading fingers.

12. The vertebral spreading instrument as set forth in claim 1, wherein the at least two additional markers are configured to reflect or emit infrared light or sound waves.

13. The instrument navigation system as set forth in claim 7, further comprising at least two additional markers configured to reflect or emit detection beams or detection waves.

14. A vertebral spreading instrument comprising:
   a plurality of spreading fingers; and
   a spreading mechanism operatively coupled to the plurality of spreading fingers, the spreading mechanism operable to adjust a spacing between the spreading fingers, wherein the spreading mechanism includes:
   a first part;
   a first trackable marker attached to the first part configured to reflect or emit detection beams or detection waves;
   an elongated member coupled to the first part and operable to move relative to the first part;

a second part coupled to the elongated member, the second part having a variable configuration, wherein movement of the elongated member relative to the first part effects a configuration change of the second part, thereby effecting a corresponding adjustment of the spreading fingers; and a second trackable marker attached to the second part configured to reflect or emit detection beams or detection waves;

wherein the first part includes a gap such that when moving the second part the second trackable marker moves along the gap.

15. The vertebral spreading instrument as set forth in claim 14, further comprising at least two additional markers configured to reflect or emit detection beams or detection waves.

* * * * *